United States Patent [19]
Silva

[11] Patent Number: 5,573,397
[45] Date of Patent: Nov. 12, 1996

[54] METHOD FOR CREATING A UNIVERSAL MOUNT FOR DENTAL ARTICULATORS

[75] Inventor: Robert Silva, Lakewood, Colo.

[73] Assignee: S-Tec, Inc., Lakewood, Colo.

[21] Appl. No.: 310,921

[22] Filed: Sep. 21, 1994

Related U.S. Application Data

[63] Continuation-in-part of Ser. No. 85,812, Jul. 6, 1993, Pat. No. 5,352,117.

[51] Int. Cl.$^6$ .................................................. A61C 11/00
[52] U.S. Cl. ................................................. 433/56; 433/54
[58] Field of Search ........................... 433/54, 56, 60, 433/72, 213

[56] References Cited

U.S. PATENT DOCUMENTS

| | | |
|---|---|---|
| 2,629,929 | 3/1953 | Levine et al. |
| 3,159,914 | 12/1964 | De Pietro ................. 433/56 |
| 3,160,955 | 12/1964 | De Pietro ................. 433/56 |
| 3,750,289 | 8/1973 | Guichet ................... 433/56 |
| 3,937,773 | 2/1976 | Huffman ................... 264/17 |
| 4,122,606 | 10/1978 | Roman. |
| 4,368,042 | 1/1983 | Felstead et al. ........... 433/213 |
| 4,371,339 | 2/1983 | Zeiser ..................... 433/74 |
| 4,398,884 | 8/1983 | Huffman ................... 433/74 |
| 4,439,151 | 3/1984 | Whelan .................... 433/60 |
| 4,459,110 | 7/1984 | Jackson ................... 433/74 |
| 4,462,801 | 7/1984 | Lagios .................... 433/60 |
| 4,538,987 | 9/1985 | Weissman .................. 433/60 |
| 4,600,385 | 7/1986 | Lee ....................... 433/60 |
| 4,608,016 | 8/1986 | Zeiser .................... 433/74 |
| 4,721,463 | 1/1988 | Lee ....................... 433/54 |
| 4,721,464 | 1/1988 | Roden et al. .............. 433/74 |
| 4,767,330 | 8/1988 | Burger .................... 433/213 |
| 4,767,331 | 8/1988 | Hoe ....................... 433/213 |
| 5,087,197 | 2/1992 | Sullivan .................. 433/74 |
| 5,197,874 | 3/1994 | Silva ..................... 433/60 |
| 5,352,117 | 10/1994 | Silva .................... 433/74 |

FOREIGN PATENT DOCUMENTS

| | | | |
|---|---|---|---|
| 2922045 | 12/1980 | Germany | 433/60 |
| 2923208 | 12/1980 | Germany | 433/60 |
| 3315870 | 11/1984 | Germany | 433/60 |
| WO88/10101 | 12/1988 | WIPO. | |

OTHER PUBLICATIONS

*Fundamentals of Fixed Prosthodontics*, Herbert T. Shillingburg, Jr. D.D.S., Sumiya Hobo, D.D.S., Lowell D. Whitsett, D.D.S., Quintessence Publishing Co., Inc. (1978); Title page, pp. 55–58 and pp. 224–228.

Zahn Dental Company, Inc., 1993 catalog; cover page and pp. 43–46.

LMT, Lab Management Today, Apr., 1994; cover page and pp. 29–36.

*Primary Examiner*—Nicholas D. Lucchesi
*Attorney, Agent, or Firm*—Gary M. Polumbus; Holland & Hart LLP

[57] ABSTRACT

A technique for creating "universally" calibrated dental articulators includes using a replica which simulates upper and lower dental models of a patient to properly align mounting plates to an articulator. The mounting plates are releasably attached to the replica before upper and lower frame members of the articulator are closed about the replica and fixed to the mounting plates. The replica is then detached from the mounting plates and used to form additional articulators identically calibrated with mounting plates. Base plates releasably attachable to the mounting plates are then used to form and mount the dental models. A first base plate is fixed to a first dental model and is then releasably attached to a mounting plate on the articulator. A second base plate is then releasably attached to the opposing mounting plate on the articulator. A second dental model is then either formed on or attached to the second base plate so that the first and second dental models are properly aligned when the upper and lower frame members of the articulator are closed. Once the upper and lower dental models have been formed on the calibrated articulator, the base plates fixed to the dental models may be removed from the mounting plates and transferred to another "universally" calibrated articulator while maintaining proper alignment between the upper and lower models.

10 Claims, 4 Drawing Sheets

METHOD FOR CREATING A UNIVERSAL MOUNT FOR DENTAL ARTICULATORS

CROSS-REFERENCE TO RELATED APPLICATION

This is a continuation-in-part of application Ser. No. 08/085,812, filed Jul. 6, 1993, now U.S. Pat. No. 5,352,117 for METHOD AND APPARATUS FOR ATTACHING A DENTAL MODEL TO AN ARTICULATOR, which is assigned to the assignee hereof. The disclosure of the parent application is incorporated herein by this reference.

BACKGROUND OF THE INVENTION

This invention relates to mounting dental models on articulators, and more particularly to preparing a number of dental articulators in a uniform fashion so that separate upper and lower dental models may be interchangeably mounted on the different articulators while still maintaining a proper alignment between the upper and lower models.

Formerly, it was common for dental models to be fixed to an articulator so that work on the dental models was done while the models were attached to the articulator. Recent advances have allowed dental models to be removably attached to articulators so that work on the dental model (such as the processing of a dental prosthesis) can be accomplished while the model is separated from the articulator. Following processing, the dental model could then be reattached to the articulator so that the fit of the dental prosthesis and the relationship between the opposing dental models could be reviewed. Such a system for removably attaching a dental model to an articulator is shown in parent application Ser. No. 08/085,812, filed Jul. 6, 1993, for METHOD AND APPARATUS FOR ATTACHING A DENTAL MODEL TO AN ARTICULATOR.

Even with the above-noted advances for mounting dental models to articulators, dental labs and technicians are still hampered by the problem that, once mounted to a certain articulator, the dental prosthesis and models must remain with that particular articulator to preserve the proper relationship and alignment between the upper and lower dental models. Thus, dental labs typically utilize inexpensive or disposable articulators when fashioning and mounting a dental model so that the articulator can be sent to the dentist along with the dental prosthesis to allow the dentist to properly review the working relationship between the prosthesis and the upper and lower dental models. Frequently, these disposable articulators are not adjustable and are capable of only a hinge opening.

The use of such inexpensive or disposable articulators necessarily reduces the accuracy with which the movements of a patient's jaw can be reproduced, and thus reduces the accuracy with which the dental prosthesis can be fabricated. While it would be desirable to use fully adjustable articulators in the preparation of a dental prosthesis, the cost of such an articulator would likely be prohibitive since the articulator must be sent by the dental lab to the dentist along with the models and the prosthesis.

It is against this background that even further significant improvements and advancements have evolved in the field of systems for removably attaching a dental model to an articulator.

SUMMARY OF THE INVENTION

One of the significant aspects of the present invention is a method of mounting dental models to calibrated articulators so that the dental models can be positioned correctly on different articulators.

Another significant aspect of the present invention relates to the fact that a large number of articulators may be identically calibrated so that they may be used interchangeably with one another when mounting dental models formed on any one of the articulators.

A further significant aspect of the present invention relates to a standardized replica shaped to simulate a patient's dental models and used to calibrate the articulators.

A still further significant aspect of the present invention is that the method of calibrating the articulators can be used with a large number of currently available articulator designs.

These and other significant aspects and advantages are provided by the method of the present invention. The method provides for forming a replica which simulates a patient's opposing upper and lower dental models. The replica is used for the purpose of fixing mounting plates to upper and lower frame members of an articulator so that the mounting plates are properly aligned on the articulator.

The replica also preferably simulates opposing base plates attached to the simulated dental models. The simulated base plates allow the replica to be releasably attached to the mounting plates. Once the mounting plates are releasably attached, the replica is positioned between the upper and lower frame members of the articulator which are then closed about the mounting plates until the frame members are substantially parallel to one another. The upper and lower frame members are then fixed to the mounting plates as by an adhesive material. Finally, the replica is detached from the mounting plates, leaving behind the articulator and the attached mounting plates. The replica may then be used to form a number of identically calibrated articulators.

Mounting dental models to the calibrated articulators entails using base plates (corresponding to the simulated base plates on the replica) in the formation of the dental models. Once a first dental model is formed and fixed to a first base plate, the first base plate is releasably attached to the mounting plate on the corresponding (either upper or lower) frame member of the articulator. Next, a second base plate is releasably attached to the opposing mounting plate (either lower or upper) on the articulator. The opposing second dental model (either lower or upper) is then aligned with the first dental model and the articulator is closed so that the frame members of the articulator are substantially parallel to one another. The second dental model is then fixed to the second base plate as by applying an adhesive between the second dental model and the second base plate prior to closing the articulator. If the second dental model has not previously been formed, the negative dental mold for the second dental model may be positioned atop the first dental model and filled with uncured dental stone. The opposing articulator frame member is then closed so that the second base plate is immersed within the uncured dental stone in the negative dental mold. Once the dental stone hardens, the negative mold may be removed so that both dental models are fixed to their respective base plates which, in turn, are releasably attached to the mounting plates fixed to the articulator.

Once a patient's upper and lower dental models have been formed on one of the "universally" calibrated articulators, the base plates fixed to the dental models may be removed from the mounting plates of the articulator and transferred to a different "universally" calibrated articulator while maintaining the proper alignment between the upper and lower models.

A more complete appreciation of the present invention and its scope can be obtained from understanding the accompanying drawings, which are briefly summarized below, the following detailed description of a presently preferred embodiment of the invention, and the appended claims.

DETAILED DESCRIPTION OF THE INVENTION

Figure 1:
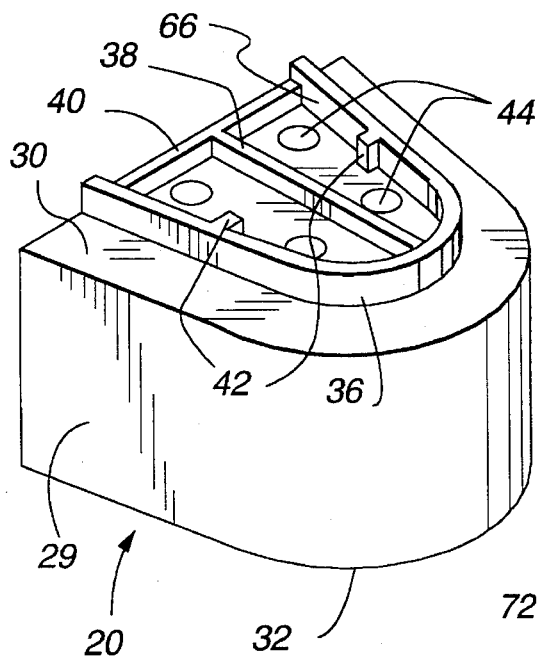
FIG. 1 is an isometric view of a dental replica embodying the present invention.
Figure 6:
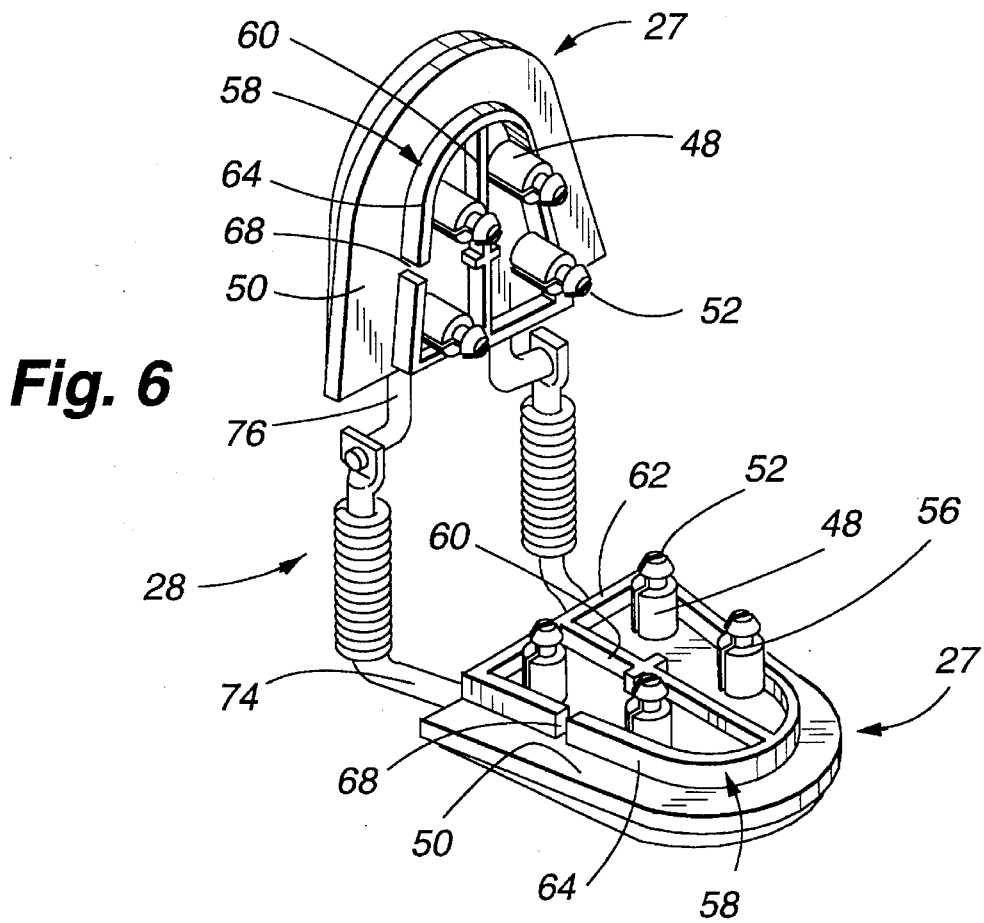
FIG. 6 is an isometric view of the articulator illustrated in FIG. 4, showing the frame members of the articulator in an open position and the mounting plates separated from the replica.
Figure 7:
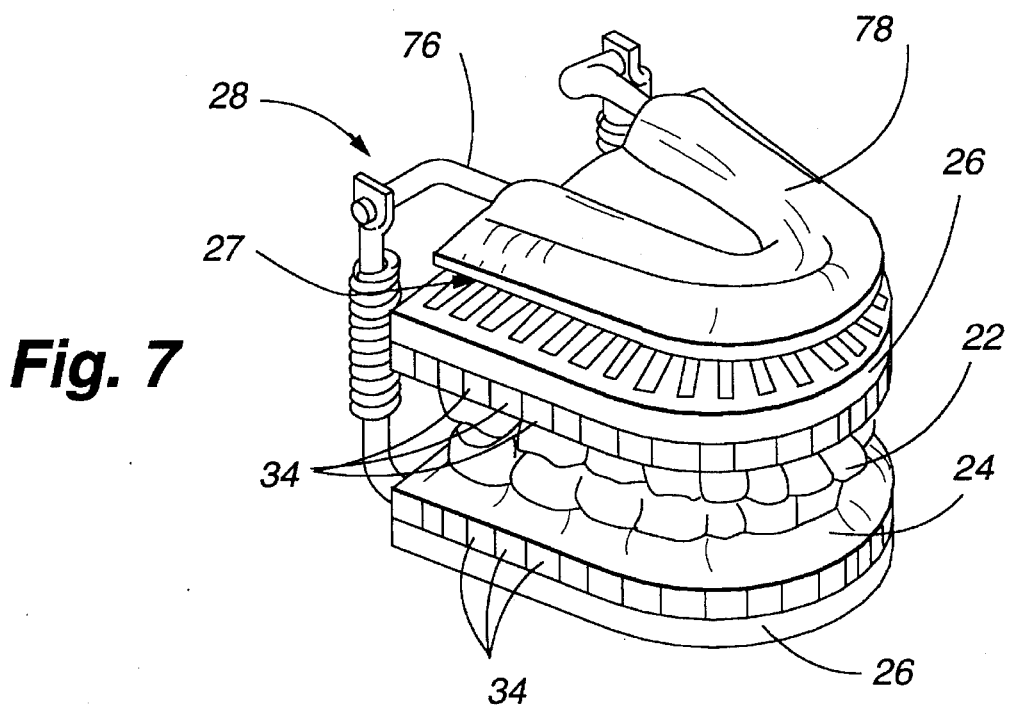
FIG. 7 is an enlarged isometric view showing the mounting plates on the articulator attached to separate base plates which support upper and lower dental models.
Figure 8:
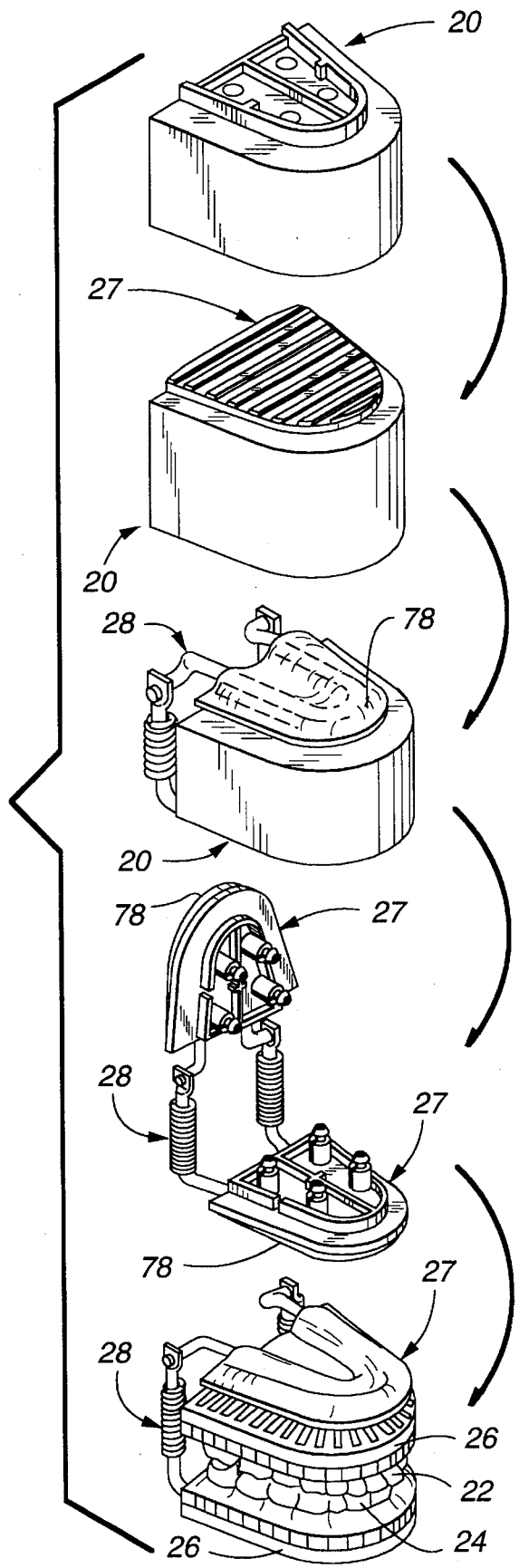
FIG. 8 is an exploded isometric view illustrating the steps of the present invention for calibrating the articulator.

FIGS. 1 and 8 show a replica 20 which is used in the method of the present invention to simulate both a combination of upper and lower dental models 22 and 24 (FIG. 7), in addition to separate base plates 26 attached to the dental models as shown in FIG. 7. The base plates 26 used to hold the dental models 22 and 24 are discussed below and are described in detail in U.S. Pat. No. 5,197,874, which disclosure is incorporated herein by reference. The replica 20 simulates the base plates 26 and dental models 22 and 24 for the purpose of fixing mounting plates 27 to articulator 28 (FIGS. 3 and 4), as described below and as shown in FIG. 8. The replica 20 assures proper alignment of the mounting plates on the articulator (FIGS. 6 and 8) so that dental models 22 and 24 and their corresponding base plates 26 may be correctly attached to the articulator (FIGS. 7 and 8).

The replica 20 is preferably molded of a suitable durable plastic material by conventional molding techniques of the plastics industry, and has an arcuate shape like the dental models and base plates which it simulates. The replica 20 includes a central portion 29 which simulates both the upper and lower dental models of a patient in a closed or confronting relationship, as shown in FIG. 7. Top and bottom surfaces 30 and 32 (FIG. 1), respectively, of the replica 20 include integral simulations of upper and lower base plates as shown in FIG. 7. The actual base plates 26 (FIG. 7) are preferably attached to the dental models 22 and 24 by a plurality of mounting blocks 34 releasably securable to the base plates. The base plates 26 and mounting blocks 34 are more fully described in U.S. Pat. No. 5,197,874.

The integral base plate simulations on the top and bottom surfaces 30 and 32 of the replica 20 (FIG. 1) preferably include a raised arcuate wall 36, a raised center-line wall 38 and a raised rear wall 40, along with a pair of raised transverse alignment tongues 42, each wall and tongue corresponding to identical components on the base plate disclosed in parent application No. 08/085,812. Similarly, the replica 20 includes a plurality of apertures 44 on both its top and bottom surfaces 30 and 32, respectively, within the perimeter of the walls 36 and 40. The apertures 44 are positioned to match the location of the apertures within the base plate shown in parent application No. 08/085,812 (which refers to the apertures 44 as "bores").

Figure 2:
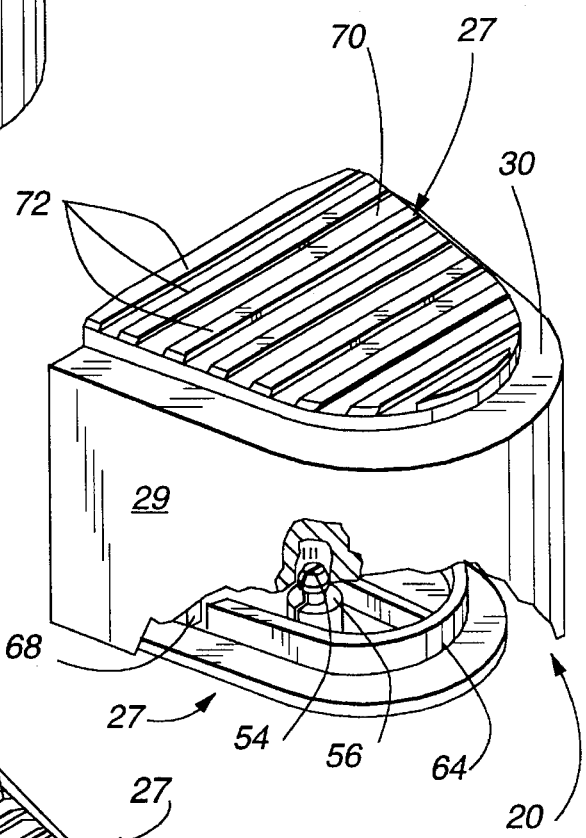
FIG. 2 is an enlarged isometric view illustrating the dental replica of FIG. 1 with mounting plates attached to top and bottom surfaces of the replica, and with parts removed for clarity.

The walls 36, 38 and 40, alignment tongues 42 and apertures 44 on the replica 20 allow identical mounting plates 27 to be snugly yet releasably attached to the top and bottom surfaces 30 and 32 of the replica, as shown in FIG. 2. The preferably plastic mounting plates 27 are best shown in FIG. 6, and the function of the mounting plates (with respect to attaching the mounting plate 27 to a base plate 26) is described in detail in parent application No. 08/085,812, which refers to the mounting plates as "adapter" plates. The connection between the mounting plate 27 and the replica 20 is briefly summarized below, and it should be understood (from the incorporation of the disclosure of parent application No. 08/085,812) that the mounting plate 27 is connected to the base plate 26 in a similar fashion.

Figure 5:
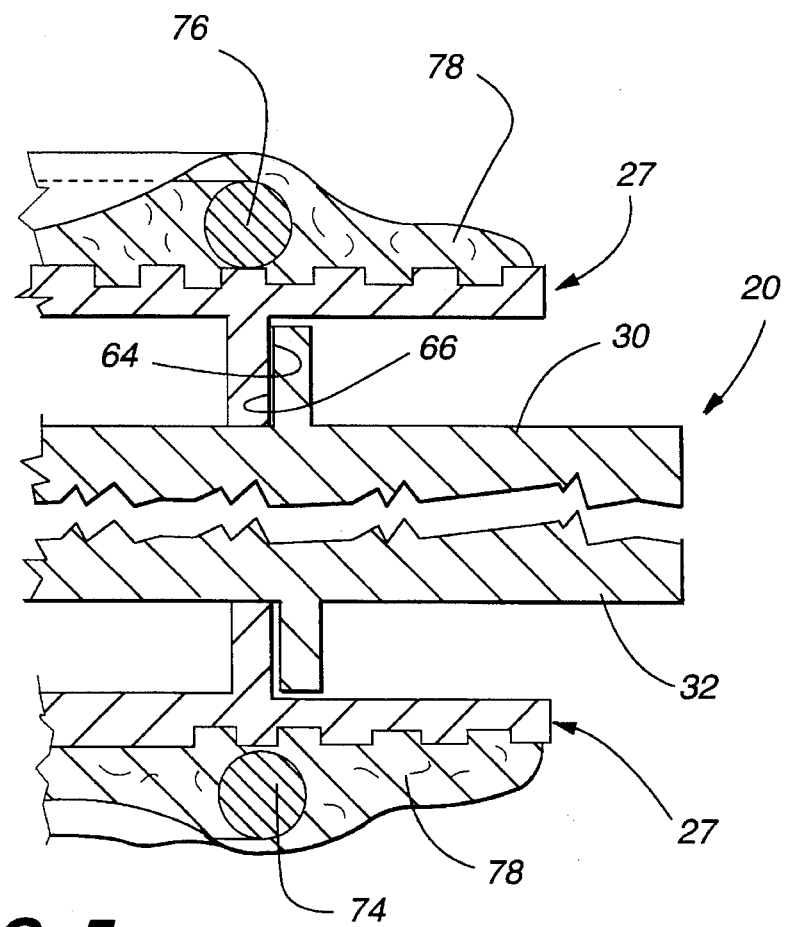
FIG. 5 is an enlarged partial section taken substantially in the plane of line 5—5 on FIG. 4.

Mounting posts 48 (FIG. 6) positioned to align with the apertures 44 in the replica 20 protrude from a first side 50 of the mounting plates 27 and include at their ends a resilient latching tab 52 with a cam surface 54 (FIGS. 2 and 6) adapted to be snapped into releasable locking engagement within the apertures 44. Each resilient latching tab 52 extends from a flat annular surface 56 of the mounting post 48, and the flat annular surface 56 is adapted to abut a flat surface around the perimeter of the aperture 44 once the latching tab 52 is inserted into the aperture. Additionally, the mounting plate 27 includes an arcuate wall 58, a center-line wall 60 and a rear wall 62 similar to those on the replica 20. An outer surface 64 of the arcuate wall 58 of the mounting plate 27 is adapted to snugly engage an inside surface 66 of the arcuate wall 36 on the replica 20 as shown in FIG. 5, while transverse slots 68 within the arcuate wall 58 of the mounting plate are adapted to fit over and receive each of the raised transverse alignment tongues 42 on the replica 20. Furthermore, the rear wall 62 and the center-line wall 60 on the mounting plates 27 are adapted to abut the rear and center-line walls 40 and 38, respectively, on the replica 20.

The cammed resilient latching tab 52 and the annular abutment surface 56 on the mounting posts 48 combine to provide a sufficient frictional engagement to firmly hold the mounting plate 27 to the replica 20, while still allowing the mounting plate to be selectively separated from the replica when the tabs 52 of the mounting posts 48 are deliberately pulled from the apertures 44. Furthermore, the engagement of the arcuate wall surfaces 66 and 68 of the replica and the mounting plate, respectively, in addition to the engagement of the transverse alignment tongues 42 of the replica 20 with the transverse slots 68 of the mounting plate 27, work in conjunction with the engaged mounting posts 48 and apertures 44 to prevent the mounting plate 27 and the replica 20 from twisting or moving relative to one another. As described in parent application No. 08/085,812, the mounting plate 27 works in a similar manner to releasably attach the base plate 26 and prevent the mounting plate and base plate from twisting or moving relative to one another.

Figure 3:
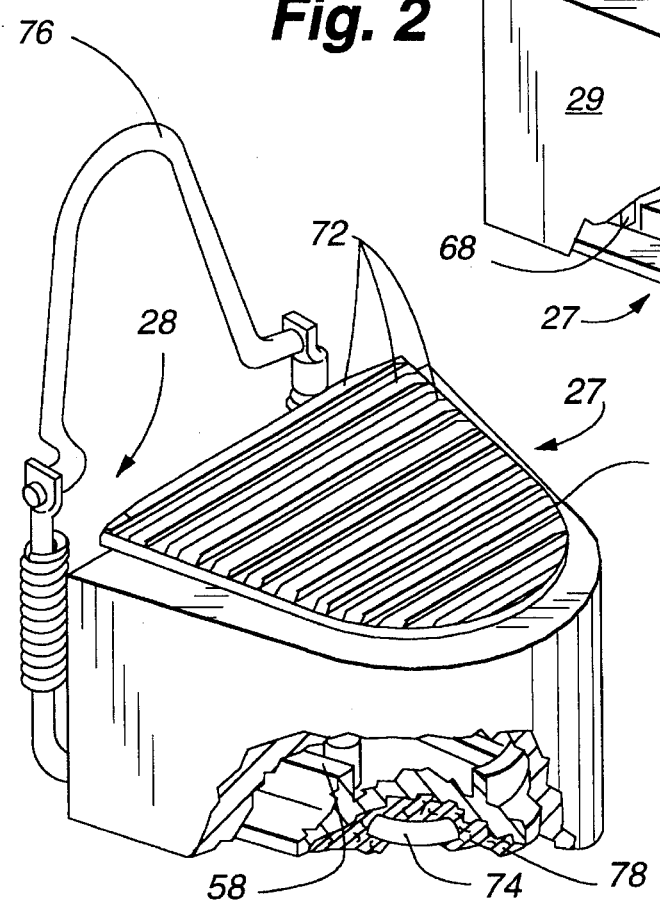
FIG. 3 is an enlarged isometric view similar to FIG. 2 illustrating a lower frame member of an articulator bonded to the mounting plate attached to the bottom surface of the replica, with parts removed for clarity.
Figure 4:
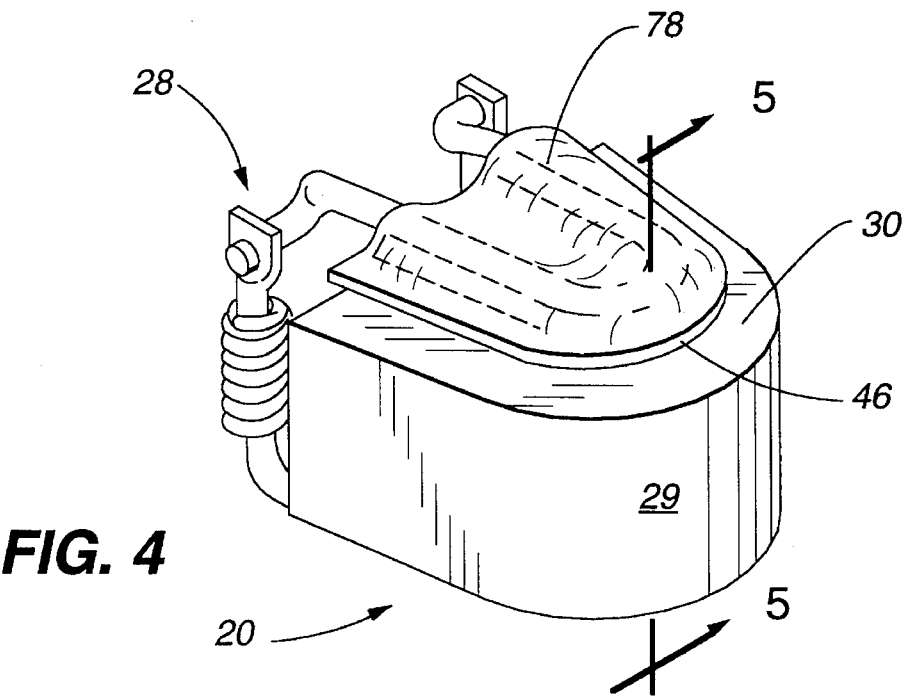
FIG. 4 is an isometric view illustrating an upper frame member of the articulator bonded to the mounting plate attached to the top surface of the replica.

A second side 70 (FIGS. 2 and 3) of the mounting plates 27, opposite the mounting posts 48, is preferably textured or roughened such as by the addition of lateral ribs 72 to enhance the application of an adhesive bonding material to the plastic surface, as shown in FIG. 5. Once the opposing mounting plates 27 have been releasably attached to the replica 20 (FIG. 2), the mounting plates 27 are bonded to lower and upper frame members 74 and 76, respectively, of an articulator 28. As shown in FIG. 3, the mounting plate 27 attached to the bottom surface 32 of the replica 20 is bonded to the lower frame member 74 of the articulator 28. While any suitable adhesive 78 may be used (such as the hot-melt wax adhesive well known in the art), plaster or an epoxy cement is preferably used to ensure a long-lasting and durable bond between the mounting plates 27 and the articulator 28. After bonding the lower frame member 74 of the articulator 28 to a mounting plate 27, the upper frame member 76 is lowered into place and similarly bonded to the mounting plate 27 attached to the top surface 30 of the replica 20 as shown in FIG. 4. Once the adhesive material 78 has dried, the replica 20 may be separated from the articulator 28 by opening the articulator frame members and pulling the mounting posts 48 from the apertures 44. Because the replica 20 is a single unit (as opposed to two separate dental models 22 and 24), the articulator 28 and replica 20 are preferably separated by first detaching the mounting plate 27 which is closest to the hinge axis of the articulator 28. Thus, with the articulator 28 shown in FIG. 4, the top mounting plate should be detached first to prevent damaging the mounting posts 48 on the lower mounting plate. As shown in FIG. 6, the articulator 28 now has mounting plates 27 permanently mounted to its lower and upper frame members 74 and 76, respectively.

The articulator 28 and mounting plates 27 (FIG. 6) may now be used to mount dental models 22 and 24 on base plates 26 (FIG. 7), as described below. The entire sequence of using the replica 20 to calibrate the articulator 28 and mount dental models 22 and 24 is shown in FIG. 8. The process of using the articulator 28 and mounting plates 27 in conjunction with two base plates 26 to form upper and lower dental models 22 and 24, respectively, while explained in detail in U.S. Pat. No. 5,197,874 and parent application No. 08/085,812, is briefly summarized below. A negative dental impression (not shown) of a patient's upper or lower teeth (typically made by a dentist and sent to the dental lab) is filled with uncured dental casting stone, and anchor tabs (not shown) protruding from the mounting blocks 34 of the base plate 26 are immersed in the uncured stone material. Once the stone material hardens about the anchor tabs, the negative dental impression is removed to provide a dental model of either the patient's upper or lower teeth fixed to the base plate 26. The side of the base plate 26 opposite the dental model is then snapped onto the corresponding (either upper or lower) mounting plate 27 which has been previously fixed to the articulator 28 using the replica 20 as described above. When forming the opposing (either lower or upper) dental model, the articulator 28 is situated so that the base plate 26 and the previously attached dental model (either upper or lower) are on the bottom and the replicated teeth of the dental model are pointing upward. Next, a blank base plate 26 is snapped onto the remaining mounting plate 27 which has also been previously fixed to the articulator 28 as described above. A negative dental impression (not shown) of the patient's opposing teeth (either lower or upper) is then precisely placed atop the first dental model and is filled with uncured dental stone. The articulator 28 is then closed until the lower and upper frame members 74 and 76 of the articulator are substantially parallel with one another and the anchor tabs (not shown) on the blank base plate 26 are immersed in the wet stone material. The negative impression is removed once the stone material of the opposing dental model has hardened.

Should one or both of the dental models (22 and 24) have been formed previously (e.g., by a dentist who did not use the base plates 26 when forming the models), the system of the present invention may still be used in the following manner: fixing one of the pre-formed dental models to a blank base plate 26 (such as by applying dental stone between the dental model and the base plate 26); releasably attaching that base plate 26 to the corresponding mounting plate 27 (either upper or lower) fixed to the articulator 28; precisely positioning the opposing pre-formed dental model atop the first dental model; snapping a blank base plate 26 to the remaining mounting plate 27 (either lower or upper); applying uncured dental stone to the opposing pre-formed dental model and closing the articulator 28 as described above so that the frame members 74 and 76 of the articulator are substantially parallel and the anchor tabs (not shown) on the blank base plate 26 are immersed in the uncured dental stone on the opposing dental model. The procedure for forming dental models (22 and 24) from negative impressions is well known in the art and the attachment of the base plates 26 to dental models is described more fully in U.S. Pat. No. 5,197,874.

Once the opposing dental models (22 and 24) have been fixed to the base plates 26 as described above, the base plates 26 and the attached models may be removed from and reattached to the mounting plates 27 fixed to the articulator 28 (such as during processing of the applicable dental prosthesis). Although the dental models can always be removed and reattached to the same articulator 28 while maintaining a proper alignment and relationship between the models (because the mounting plates 27 are fixed to the articulator 28), it was not previously possible to attach dental models to a different articulator while preserving the correct relationship and alignment between the opposing models (22 and 24). For this reason, dental labs commonly send articulators to the dentist along with the dental models and the dental prosthesis. However, by using the same (or an identical) replica 20, a number of articulators 28 may be "premounted" with mounting plates 27 so that all of said articulators 28 will operate within the same parameters which are set by the replica 20. Thus, articulators 28 prepared as described above are interchangeable with one another, and dental models formed on one articulator can be correctly and quickly mounted on a different articulator having mounting plates 27 that were fixed or "calibrated" using the same replica 20.

Although most of the operational parameters of the calibrated articulator 28 (i.e., its range of movement) will remain constant even when used with varying dental models, one parameter which may vary between cases is the vertical height of the patients' teeth (often referred to as the "incisal guidance"height). Many articulators include an adjustment referred to as an incisal guidance pin (not shown) to vary the vertical height between the lower and upper frame members 74 and 76 of the articulator. Such an incisal guidance pin is shown in U.S. patent application Ser. No. 08/245,618 filed May 19, 1994, for DENTAL ARTICULATOR and assigned to the assignee hereof. However, even when the method of the present invention is used with articulators having no adjustment for vertical height (as shown in FIGS. 3–7), the replica 20 can establish a range of motion for the calibrated articulator 28 that accurately simulates the movement of an average patient's jaw. Furthermore, adjustments can be made during the formation of the dental models to vary the height of the dental models and ensure that the frame members 74 and 76 of the articulator 28 are substantially parallel to one another when the dental models 22 and 24 are in a closed position (in contact with one another). For example, the amount of dental stone used to form the dental models 22 and 24 and to fix the dental models to the base plates 26 can be varied so that the frame members 74 and 76 of the articulator 28 are in substantially the same position as when the replica 20 was used to bond the frame members 74 and 76 to the mounting plates 27.

The benefits of forming a plurality of "universally calibrated" articulators 28 from a single replica 20 are numerous. First, once the mounting plates 27 are permanently fixed to the articulator 28, the dental models 22 and 24 need only be mounted on base plates 26 as described above for easy attachment to and quick detachment from the articulator 28. Furthermore, the number of articulators needed within a dental laboratory may be dramatically reduced since a patient's dental models need no longer remain with a single articulator throughout the period of processing the dental prosthesis. Instead, a small number of articulators (or even a single articulator 28) may be used to articulate (at different times) a large number of dental models.

However, the most significant benefit of the present invention is that dental labs need not send an articulator to the dentist along with each patient's dental models and dental prosthesis. Rather, the dental lab could send each of its dentist clients a single articulator 28 which was "premounted" with mounting plates 27 using a replica 20 as described above. Provided the dental lab uses only articulators 28 prepared using the same (or an identical) replica 20, dental models (22 and 24) formed on the articulators 28 within the dental lab may be correctly mounted on the articulator 28 at the dentist's office. Thus, a great savings can be realized by a dental lab sending each client a single high quality articulator as opposed to a large number of inexpensive or disposable articulators.

Although the replica 20 is preferably used to calibrate the articulator 28, it should be understood that the present invention pertains to the method of forming and calibrating a "universal" articulator. Accordingly, it is intended that the present invention should not be limited to the use of the replica 20 to calibrate the articulator 28. Indeed, one could use previously formed dental models attached to base plates 26 and fix them together to form an alternative "replica" for use in calibrating a number of articulators in the above-described manner. Such an alternative "replica" would function identically to the replica 20 since the replica 20 is preferably molded to simulate actual dental models and base plates. The advantage of the plastic replica 20 over an alternative "replica" formed from actual dental models is the durability and reproducibility of the molded replica 20. Since all "universally" calibrated articulators must be formed on the same (or an identical) replica, it is desirable to use the molded replica 20 which can be easily and exactly replaced if it is lost or damaged.

A presently preferred embodiment of the present invention and many of its improvements have been described with a degree of particularity. This description has been made by way of preferred example and is based on a present understanding of knowledge available regarding the invention. It should be understood, however, that the scope of the present invention is defined by the following claims, and not necessarily by the detailed description of the preferred embodiment.

The invention claimed is:

1. A method of mounting dental models on a calibrated articulator movable between open and closed positions, comprising the steps of:

releasably attaching identical mounting plates to a replica of upper and lower dental models;

fixing the mounting plates to opposing upper and lower frame members of the articulator when said frame members are in a closed position substantially parallel to one another;

detaching the replica from the mounting plates;

releasably attaching a first dental model to the mounting plate fixed to one of said upper or lower frame members of the articulator;

releasably attaching a base plate to the mounting plate fixed to the other of said upper or lower frame members of the articulator; and fixing a second dental model to the base plate so that said first and second dental models are properly aligned with one another when the upper and lower frame members of the articulator are in the closed position.

2. A method as defined in claim 1, further comprising the step of:

using the replica to prepare at least one additional calibrated articulator so that the first and second dental models can be releasably attached to the mounting plates on said additional calibrated articulator while maintaining proper alignment between the first and second dental models.

3. A method of mounting dental models on a calibrated articulator movable between open and closed positions, comprising the steps of:

releasably attaching identical mounting plates to a replica of upper and lower dental models;

positioning the replica and attached mounting plates between opposing upper and lower frame members of the articulator;

fixing the mounting plates to the upper and lower frame members when said frame members are in a closed position substantially parallel to one another;

detaching the replica from the mounting plates fixed to the upper and lower frame members of the articulator;

fixing a first dental model to a first base plate;

releasably attaching the first base plate to the mounting plate fixed to one of said upper or lower frame members of the articulator;

releasably attaching a second base plate to the mounting plate fixed to the other of said upper or lower frame members of the articulator; and fixing a second dental model to the second base plate so that said first and second dental models are properly aligned with one another when the upper and lower frame members of the articulator are in the closed position.

4. A method as defined in claim 3, further comprising the step of:

using the replica to prepare at least one additional calibrated articulator so that the first and second base plates with the respectively attached first and second dental models can be releasably attached to the mounting plates on said additional calibrated articulator while maintaining proper alignment between the first and second dental models.

5. A method of mounting upper and lower dental models on a calibrated articulator while maintaining proper alignment between said upper and lower dental models, said articulator being movable between open and closed positions, and said method comprising the steps of:

forming a replica having a central portion to simulate a set of upper and lower dental models in a confronting relationship, and top and bottom surfaces to simulate identical base plates attached to the simulated dental models;

releasably attaching identical mounting plates to the top and bottom surfaces of the replica;

positioning the replica and attached mounting plates between opposing upper and lower frame members of the articulator;

fixing the mounting plates to the upper and lower frame members when said frame members are in a closed position substantially parallel to one another;

detaching the top and bottom surfaces of the replica from the mounting plates fixed to the corresponding upper and lower frame members of the articulator;

fixing a first dental model to a first base plate;

releasably attaching the first base plate to the mounting plate fixed to one of said upper or lower frame members of the articulator;

releasably attaching a second base plate to the mounting plate fixed to the other of said upper or lower frame members of the articulator; and fixing a second dental model to the second base plate so that said first and second dental models are properly aligned with one another when the upper and lower frame members of the articulator are in the closed position.

6. A method as defined in claim 5, further comprising the step of:

using the replica to prepare at least one additional calibrated articulator so that the first and second base plates with the respectively attached first and second dental models can be releasably attached to the mounting plates on the additional calibrated articulator while maintaining proper alignment between the first and second dental models.

7. A method as defined in claim 5, further comprising the step of molding the replica from a durable plastic material.

8. A method of calibrating an articulator for releasably mounting different sets of dental models while maintaining a proper alignment between said dental models, said articulator having opposing upper and lower frame members and being movable between open and closed positions, said method comprising the steps of:

releasably attaching upper and lower mounting plates to a replica of a set of upper and lower dental models, said replica adapted to receive the mounting plates and uniformly align the mounting plates relative to each other;

positioning the replica and said mounting plates releasably attached thereto between the opposing upper and lower frame members of the articulator;

fixing the mounting plates to the upper and lower frame members when said frame members are in the closed position substantially parallel to one another; and detaching the replica from the mounting plates fixed to the upper and lower frame members of the articulator, thereby leaving the mounting plates fixedly aligned relative to each other on the articulator such that the dental models can be uniformly mounted on any articulator calibrated in the same manner.

9. A method as defined in claim 8, further comprising the step of:

forming the replica to include a central portion to simulate a set of upper and lower dental models in a confronting relationship, and top and bottom surfaces for releasable attachment to the mounting plates.

10. A method as defined in claim 9, further comprising the step of molding the replica from a durable plastic material.

* * * * *